United States Patent [19]
Picataggio et al.

[11] Patent Number: 5,254,466
[45] Date of Patent: Oct. 19, 1993

[54] SITE-SPECIFIC MODIFICATION OF THE CANDIDA TROPICALS GENOME

[75] Inventors: Stephen Picataggio, Santa Rosa; Kristine Deanda, Graton; L. Dudley Eirich, Santa Rosa, all of Calif.

[73] Assignee: Henkel Research Corporation, Santa Rosa, Calif.

[21] Appl. No.: 432,091

[22] Filed: Nov. 6, 1989

[51] Int. Cl.[5] .......................... C12N 15/09; C12P 7/44
[52] U.S. Cl. ................................ 435/142; 435/172.1; 435/172.3; 435/924; 435/254.22
[58] Field of Search .................... 435/67.1, 142, 172.3, 435/172.1, 940, 255, 924; 935/22, 28

[56] References Cited

U.S. PATENT DOCUMENTS 4,735,901  4/1988  Kurtz et al. ...................... 435/172.3

FOREIGN PATENT DOCUMENTS 183070  4/1986  European Pat. Off. .

OTHER PUBLICATIONS

Okazaki et al. Gene 57:37-44 (1987).
Okazaki et al. Biochem. 83:1232-1236 (1986).
Kelly et al. Mol. Cell. Biol. Jan 1987: p. 199-207.
Gillam et al. Mol. Gen. Genet. 198: 179 (1984).
Stromnaes et al. J. Bact. Jan. 1986: 197.
Ditchburn et al. J. Gen Microbiol. 67:299 (1971).
Gaillasdin et al. Chem Abst. vol. 77 (23) No. 149584R 1971.
Watanabe et al. Chem. Abst. vol. 70 (15) No. 65372n 1968.
Small et al. J. Cell. Biol. 105:247 (1987).
*Strain and Species Identification by Restriction . . . Candida Species,* Journal of Bacteriology, Apr. 1987, pp. 1639-1643, Magee et al.
*The Genetics of Candida,* CRC Press, 1990, pp. 177-186, Kirsch et al.
*Genetics of Candida albicans,* Microbiological Reviews, Sep. 1990, pp. 226-241, Scherer et al.
*Isolation and Determination of Yeasts . . . Source of Carbon,* Agr. Biol. Chem., vol. 30, No. 12, pp. 1175-1182, 1966, Tanabe et al.
*Methods for the Genetics and Molecular Biology of Candida albicans,* Analytical Biochemistry, 175, pp. 361-372 (1988), Magee et al.
*The Genus Candida Berkhout nom. conserv. . . . Delimitation,* System. Appl. Microbiol. 12, pp. 183-190 (1989), Viljoen et al.
*Variation in the electrophoretic karyotype . . . in Candida albicans,* Journal of General Microbiology (1990), 136, pp. 2433-2442, Iwaguchi et al.
*The Carboxyl-terminal Tripeptide Ala-Lys-Ile . . . Yeast Peroxisomes,* The Journal of Biological Chemistry, vol. 266, No. 34, pp. 23197-23208, 1991, Aitchison et al.
*In vivo import of Candida tropicalis . . . Candida albicans,* Current Genetics, 1990, 17:481-486, Aitchison et al.
*Redefinition of Candida Berkhout and the consequent emendation of Cryptococcus Kuetzing and Rhodotorula Harrison,* accepted 31 Mar. 1988, Weijman et al.
*Interspecific Complementation Analysis . . . Candida albicans Adenine Auxotrophs,* Journal of Bacteriology, Jun. 1989, vol. 171, No. 6, pp. 3586-3589, Corner et al.
*Sequence and transcript analysis . . . -phosphate decarboxylase,* Curr Genet (1989), 16:153-157, Losberger et al.
*The yeasts a taxonomic study,* third edition, Elsevier Science Publishers B.V.—Amsterdam, N.J.W. Kreger-van Rij, ed.
*Differential Identification of Candida Species . . . Polypeptide Profiles,* Analytical Biochemistry 175, 548-551 (1988), Shen et al.

(List continued on next page.)

Primary Examiner—Richard A. Schwartz
Assistant Examiner—J. LeGuyader
Attorney, Agent, or Firm—Ernest G. Szoke; Wayne C. Jaeschke; John E. Drach

[57] ABSTRACT

The POX genes of *C. tropicalis* are disrupted resulting in the complete blockage of the beta-oxidation pathway in the strain. Fermentation of *C. tropicalis* cells having disrupted genes on alkane, fatty acid and fatty acid ester substrates produces substantially pure dicarboxylic acids in substantially quantitative yield.

30 Claims, 4 Drawing Sheets

OTHER PUBLICATIONS

Transformation of Intact Yeast Cells Treated with Alkali Cations, Hisao Ito, Yasuki Fukuda, Kousaku Murata and Akira Kimura, Jan. 1983, pp. 163–168.

Acyl-Coa Oxidase From *Canadida tropicalis*, Sakayu Shimizu, Koji Yasui, Yoshiki Tani and Hideaki Yamada, Nov. 14, 1979, vol. 91, No. 1, pp. 108–113.

The Regulation of Alanine on the Fermentation of Long-Chain Dicarboxylic Acids in *Candida tropicalis* NPcoN22, Zhou Jianlong, Chiao Juishen, p. 4.

Improved M13 Chage Cloning Vectors and Host Strains; Nucleotide Sequences of the M13mp 18 and pUC19 Vectors, Cleste Yanish-Perron, Jeffrey Viera and Joachim Messing, Gene 33(1985) pp. 103–119.

Inducible Long Chain Alcohol Oxidase from Alkane-grown *Candida tropicalis*, Glenwyn D. Kemp, F. Mark Dickinson and Colin Ratledge, Appl. Microbiol Biotechnol (1988) 29:pp. 370–374.

Aliphatic Hydrocarbons, Matthia Buehler, Joachim Schindler, Chapter 9, pp. 331–384.

[12] One-Step Gene Disruption in Yeast by Rodney J. Rothstein, (1981), pp. 202–211.

Interactions between the $\omega$-and $\beta$-Oxidations of Fatty Acids, Joseph Vamecoq and Jean-Pierre Draye, Jan. 27, 1987, J. Biochem 102, pp. 225–234.

Production of Macrocyclic Musk Compounds Via Alkanedioic Acids Produced from N-alkanes, LHiroshi Okina, Akira Taoka, Namio Uemura, Nov. 20, 1986, pp. 753–760.

Mircobial Production of Long-chain Dicarboxylic Acids from n-Alkanes, Part I. Screening and Properties of Microorganism Producing Dicarboxylic Acids, by Isamu Shiio and Ryosuke Uchio, Arg. Biol. Chem. vol. 35, No. 13, pp. 2033–2012 (1971).

Peroxidomal Localization of Enzymes Related to Fatty Acid $\beta$-Oxidation in an n-Alkane-grown Yeast, *Candida tropicalis*, Mitsuyoshi Ueda et al., Agric. Biol. Chem. 49(6). pp. 1821–1828 (1985).

Two Acyl-coenzyme A Oxidase in Peroxisomes of the Yeast *Candida tropicalis:* Primary Structures Deduced from Genomic DNA Sequence, Okazaki et al., Proc. Natl. Acad. Sci., USA vol. 83, pp. 1232–1236, Mar. 1986.

Studies of Utilization of Hydrocarbons by Yeasts Part II. Diterminal Oxidation of Alkanes by Yeast, Ogino et al., Agr. Biol. Chem. vol. 29, No. 11, pp. 1009–1015 (1965).

Direct Mutagenesis in *Candida albicans:* On-Step Gene Disruption to Isolate ura3 Mutents, Kelly et al., Molecular and Cellusar Biology, Jan. 1987, pp. 199–207.

Studies on the Formation of Long-chain Dicarboxylic Acids from Pure n-alkanes by a Mutant of *Candida tropicalis*, Hill et al., Appl. Microbiol Biotechnol (1986) 24:168–174.

Omega-Hydroxylations, Franz Meussdoerffer pp. 143–146, Biochem. Labs Henkel KGaA.

Degradation of Long-chain n-alkanes by the Yeast *Candida maltosa*, II. Oxidation of n-alkanes and Intermediates Using Microsomal Membrane Fractions, Blasig et al., Appl. Microbiol Biotechnol (1988) 28: pp. 589–597 (1988).

A Method for Gene Disruption that Allows Repeated Use of URA3 Selection in the Construction of Multiply Disrupted Yeast Strains, Alani et al., (1987), Genetics, 116: pp. 541–545.

A Positive Selection for Mutants Lacking Orotidine-5-'-phosphate Decarboxylase Activity in Yeast: 5--fluoro-orontic Acid Resistance, Boecke et al., Mol. Gen. Genet (1984) 197: pp. 345–346.

Mechanisms and Occurrence of Microbial Oxidation of Long-chain Alkanes, Rehm et al. Institute for Microbiologie, pp. 176–217.

*Molecular and General Genetics*, vol. 214, issued 1988, R. Kelly et al. "One-step gene disruption by cotransformation to isolate double auxotrophs in *Candida albicans*", pp. 24–31.

*Molecular and General Genetics*, vol. 217, issued Jan. 1989, M. Kurtz et al, "Isolation of *Hem3* mutants from *Candida albicans* by sequential gene disruption"pp. 47–52.

*Molecular and Cell Biology*, vol. 7, No. 1, issued Jan. 1987, R. Kelly et al., "Directed mutagenesis in *Canadida albicans:* One-step gene disruption to isolate ura3 Mutants", pp. 199–207.

*Molecular and Cellular Biology*, vol. 6, No. 1, issued Jan. 1986, M. Kurtz et al., "Integrative Transformation of (List continued on next page.)

OTHER PUBLICATIONS

*Candida albicans.* Using a Cloned Candida ADE2 Gene", pp. 142-149.

*Proceeding National Academy Science,* vol. 83, issued Mar. 1986. K. Okazaki et al.."Two acyl-coenzyme A oxidases in peroxisomes of the yeast *Candida tropicalis:* Primary structures deduced from genomic DNA sequence pp. 1232-1236.

"*Journal of Cell Biology.,* vol. 105 issued Jul. 1987., T. M. Small et al. "Export of the carboxy-terminal Portion of Acyl-CoA oxidase into Peroxisomes of *Candida tropicalis*" pp. 217-252.

*Gene,* vol. 58 issued 1987. K. Okazaki et al., "Peroxismal Acyl-coenzyme A oxidase multigene family of the yeast *Candida tropicals:* nucleotide sequence of a third gene an its protein product", pp. 37-47.

*Journal of Bacteriology,* vol. 172, No. 3 issue Aug. 1990, [O. C. Haas et al., "Development of an integrative DNA Transformation System for the yeast *Candida tropicalis*", pp. 4571-4577.

*Gene* vol. 51, issued 1987, W. W. Murray et al, "The primary structure of a peroxisomal fatty acyl-CoA oxidase from the yeast *Canada tropicalis* p K233", pp. 119-128.

*Proceeding National Academy of Science,* vol. 76 No. 10 issued Oct. 1979. S. Scherer et al. "Replacement of Chromosome Segments with altered DNA sequences constructed *in vitro*". pp. 4951-4955.

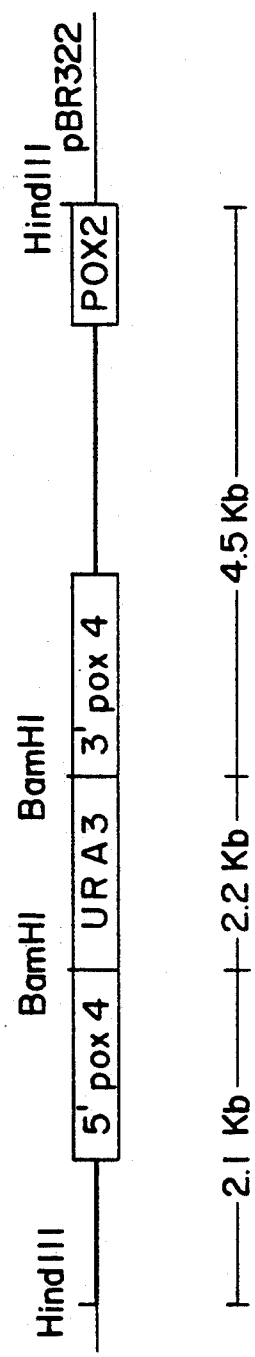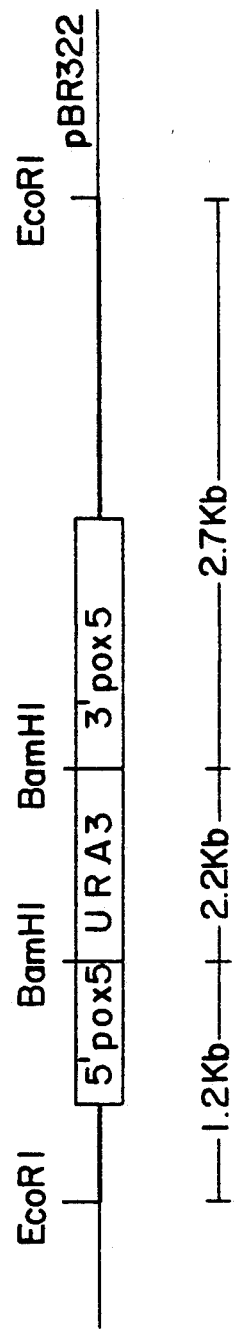
FIG. 1A
FIG. 1B

FIG. 4

LINEAGE:

| STRAIN | % BLOCK | GENOTYPE | | | |
|---|---|---|---|---|---|
| | | POX 4A | POX 4B | POX 5 | POX 5 |
| SU-2 | 0 | + | + | + | + |
| H41 | 25 | − | + | + | + |
| H41B | 25 | + | − | + | + |
| H51 | 25 | + | + | − | + |
| H45 | 50 | − | + | − | + |
| H43 | 50 | − | − | + | + |
| H53 | 50 | + | + | − | − |
| H534 | 75 | − | + | − | − |
| H534B | 75 | + | − | − | − |
| H435 | 75 | − | − | + | − |
| H5343 | 100 | − | − | − | − |

− = DISRUPTED
+ = FUNCTIONAL

SITE-SPECIFIC MODIFICATION OF THE CANDIDA TROPICALS GENOME

BACKGROUND OF THE INVENTION

1. Field of the Invention

This invention relates to a process for the highly specific modification of the genome of the yeast *Candida tropicalis*. This invention also relates to *C. tropicalis* strains with multiple POX4 and POX5 gene disruptions and to a method of using these strains for the production of dicarboxylic acids.

2. Description of the Related Art

Aliphatic dioic acids are versatile chemical intermediates useful as raw materials for the preparation of perfumes, polymers, adhesives and macrolid antibiotics. While several chemical routes to the synthesis of long-chain alpha, omega dicarboxylic acids are available, the synthesis is not easy and most methods result in mixtures containing shorter chain lengths. As a result, extensive purification steps are necessary. While it is known that long-chain dioic acids can also be produced by microbial transformation of alkanes, fatty acids or esters, chemical synthesis has remained the preferred route, due to limitations with the current biological approaches.

Several strains of yeast are known to excrete alpha, omega-dicarboxylic acids as a byproduct when cultured on alkanes or fatty acids as the carbon source. In particular, yeast belonging to the Genus Candida, such as *C. albicans, C. cloacae, C. guillermondii, C. intermedia, C. lipolytica, C. maltosa, C. parapsilosis* and *C. zeylenoides* are known to produce such dicarboxylic acids (Agr. Biol. Chem. 35: 2033-2042 (1971)). Also, various strains of *C. tropicalis* are known to produce dicarboxylic acids ranging in chain lengths from $C_{11}$ through $C_{18}$ (Okino et al., In BM Lawrence, BD Mookherjee and BJ Willis (eds), Flavors and Fragrances: A World Perspective. Proceedings of the $10^{th}$ International Conference of Essential Oils, Flavors and Fragrances, Elsevier Science Publishers BV Amsterdam (1988); and are the basis of several patents as reviewed by Bühler and Schindler, in Aliphatic Hydrocarbons in Biotechnology, H. J. Rehm and G. Reed (eds), Vol. 169, Verlag Chemie, Weinheim (1984).

It has been established that hydrocarbon substrates are enzymatically oxidized in the yeast microsomes. Following transport into the cell, n-alkane substrates for example, are hydroxylated to fatty alcohols by a specific cytochrome P450 system (Appl. Microbiol. Biotechnol., 28, 589-597 (1988)). Two further oxidation steps, catalyzed by alcohol oxidase (Kemp et al., Appl. Microbiol. and Biotechnol, 28, p370-374 (1988)) and aldehyde dehydrogenase, lead to the corresponding fatty acid. The fatty acids can be further oxidized through the same pathway to the corresponding dicarboxylic acid. The omega-oxidation of fatty acids proceeds via the omega-hydroxy-fatty acid and its aldehyde derivative, to the corresponding dicarboxylic acid without the requirement for CoA activation. However, both fatty acids and dicarboxylic acids can be degraded, after activation to the corresponding acyl-CoA ester, through the $\beta$-oxidation pathway in the peroxisomes, leading to chain shortening. In mammalian systems, both fatty acid and dicarboxylic acid products of omega-oxidation are activated to their CoA-esters at equal rates and are substrates for both mitochondrial and peroxisomal $\beta$-oxidation (J. Biochem., 102, 225-234 (1987)). In yeast, $\beta$-oxidation takes place solely in the peroxisomes (Agr. Biol. Chem., 49, 1821-1828 (1985)).

The dicarboxylic acids produced through fermentation by most yeasts, including *C. tropicalis*, are most often shorter than the original substrate by one or more pairs of carbon atoms and mixtures are common (Ogino et al., 1965; Shio and Uchio, 1971; Rehm and Reiff, 1980; Hill et al., 1986). This is due to the degradation of the substrate and product by the peroxisomal $\beta$-oxidation pathway. This series of enzymatic reactions leads to the progressive shortening of the activated acyl-CoA through the cleavage of 2 carbon acetyl-CoA moieties in a cyclic manner. The initial step in the pathway, involving oxidation of the acyl-CoA to its enoyl-CoA derivative, is catalyzed by acyl-CoA oxidase. The enoyl-CoA is further metabolized to the $\beta$-keto acid by the action of enoyl-CoA hydratase and 3-hydroxyacyl-CoA dehydrogenase as a prerequisite to the cleavage between the alpha- and beta-carbons by 3-ketoacyl-CoA thiolase. Mutations causing partial blockage of these latter reactions result in the formation of unsaturated or 3-hydroxy-monocarboxylic or 3-hydroxy-dicarboxylic acids (Meussdoeffer, 1988). These undesirable by-products are often associated with biological production of dicarboxylic acids. It is also known that the formation of dioic acids can be substantially increased by the use of suitable mutants (Shiio and Uchio, 1971; Furukawa et al., 1986; Hill et al., 1986; Okino et al., 1986). The wild-type yeasts produce little if any dicarboxylic acid. Often, mutants partially defective in their ability to grow on alkane, fatty acid or dicarboxylic acid substrates demonstrate enhanced dicarboxylic acid yields. However, these mutants have not been characterized beyond their reduced ability to utilize these compounds as a carbon source for growth. In all likelihood, their ability to produce dicarboxylic acids is enhanced by a partial blockage of the $\beta$-oxidation pathway. Furthermore, compounds known to inhibit $\beta$-oxidation (ie. acrylate) also result in increased dicarboxylic acid yields (Zhou and Juishen, 1988).

Therefore, it would be desirable to have an effective block of the $\beta$-oxidation pathway at its first reaction, catalyzed by acyl-CoA oxidase. A complete block, here, should result in enhanced yields of dicarboxylic acid by redirecting the substrate toward the omega-oxidation pathway while preventing reutilization of the dicarboxylic acid products through the $\beta$-oxidation pathway. In addition, the use of such a mutant should prevent the undesirable chain modifications associated with passage through $\beta$-oxidation, such as unsaturation, hydroxylation, or chain shortening. No mutants obtained by random mutagenesis are yet available in which this enzyme has been completely inactivated. While the *C. tropicalis* acyl-CoA oxidase genes have been cloned and sequenced (Okazaki et al., 1986) the lack of a method for the targeted mutagenesis of the *C. tropicalis* genome has prevented specific inactivation of the chromosomal acyl-CoA oxidase genes. A method for targeted gene disruption in yeast of the genus Pichia has been disclosed in European Patent Application 0 226 752. However, the present invention is the first description of targeted mutagenesis in *C. tropicalis*.

The production of dicarboxylic acids by fermentation of unsaturated $C_{14}$-$C_{16}$ monocarboxylic acids using a strain of the species *C. tropicalis* is disclosed in U.S. Pat. No. 4,474,882. The unsaturated dicarboxylic acids correspond to the starting materials in the number and position of the double bonds. Similar processes in which other special microorganisms are used are described in U.S. Pat. Nos. 3,975,234 and 4,339,536, in British Patent Specification 1,405,026 and in German Patent Publications 21 64 626, 28 53 847, 29 37 292, 29 51 177, and 21 40 133.

None of the processes mentioned above gives the desired dicarboxylic acids in quantities sufficient to be commercially viable.

SUMMARY OF THE INVENTION

One aspect of the present invention provides a process for the site-specific modification of the *C. tropicalis* genome, comprising transforming a *C. tropicalis* host cell with a linear DNA fragment comprised of a selectable marker gene, wherein said selectable marker gene is flanked on both ends by DNA sequences having homology to a chromosomal target gene or having homology to DNA sequences flanking a chromosomal target gene.

Another aspect of the present invention provides a process for restoring an auxotrophic phenotype to cells previously transformed to prototrophy with a selectable marker comprising the steps of: (a) selecting or screening for spontaneous mutations which inactivate said selectable marker to identify and isolate auxotrophic mutants derived from said previously transformed strain, (b) confirming the auxotrophic phenotype of said mutants, (c) confirming the parental genotype of said mutants by Southern hybridization to appropriate gene probes.

A further aspect of the present invention provides an alternate process for restoring an auxotrophic phenotype to cells previously transformed to prototrophy with a selectable marker comprising the steps of: (a) transforming prototrophic host cells with a non-functional selectable marker gene, which has been made non-functional by an in-vitro deletion of the central coding sequence of said gene, to produce auxotrophic mutants, (b) confirming the auxotrophic phenotype of said mutants, (c) confirming the genotype of said mutants.

Yet another aspect of the present invention provides a process for completely blocking the beta-oxidation pathway in *C. tropicalis* at its first reaction comprising disrupting the chromosomal POX4A, POX4B and both POX5 genes of a *C. tropicalis* host strain.

Still another aspect of the present invention provides a process for producing substantially pure omega-dicarboxylic acids in substantially quantitative yield comprising culturing *C. tropicalis* strain H5343 in a culture medium containing a nitrogen source, an organic substrate and a cosubstrate.

BRIEF DESCRIPTION OF THE DRAWINGS

FIG. 1A is a schematic representation of the spatial relationship of the POX4 disruption cassette.

FIG. 1B is a schematic representation of the spatial relationship of the POX5 disruption cassette.

FIG. 4 is a diagram of the lineage of the strains having blocked POX genes and the identity of the POX genes which are blocked in each strain.

DESCRIPTION OF THE PREFERRED EMBODIMENTS

Figure 2:
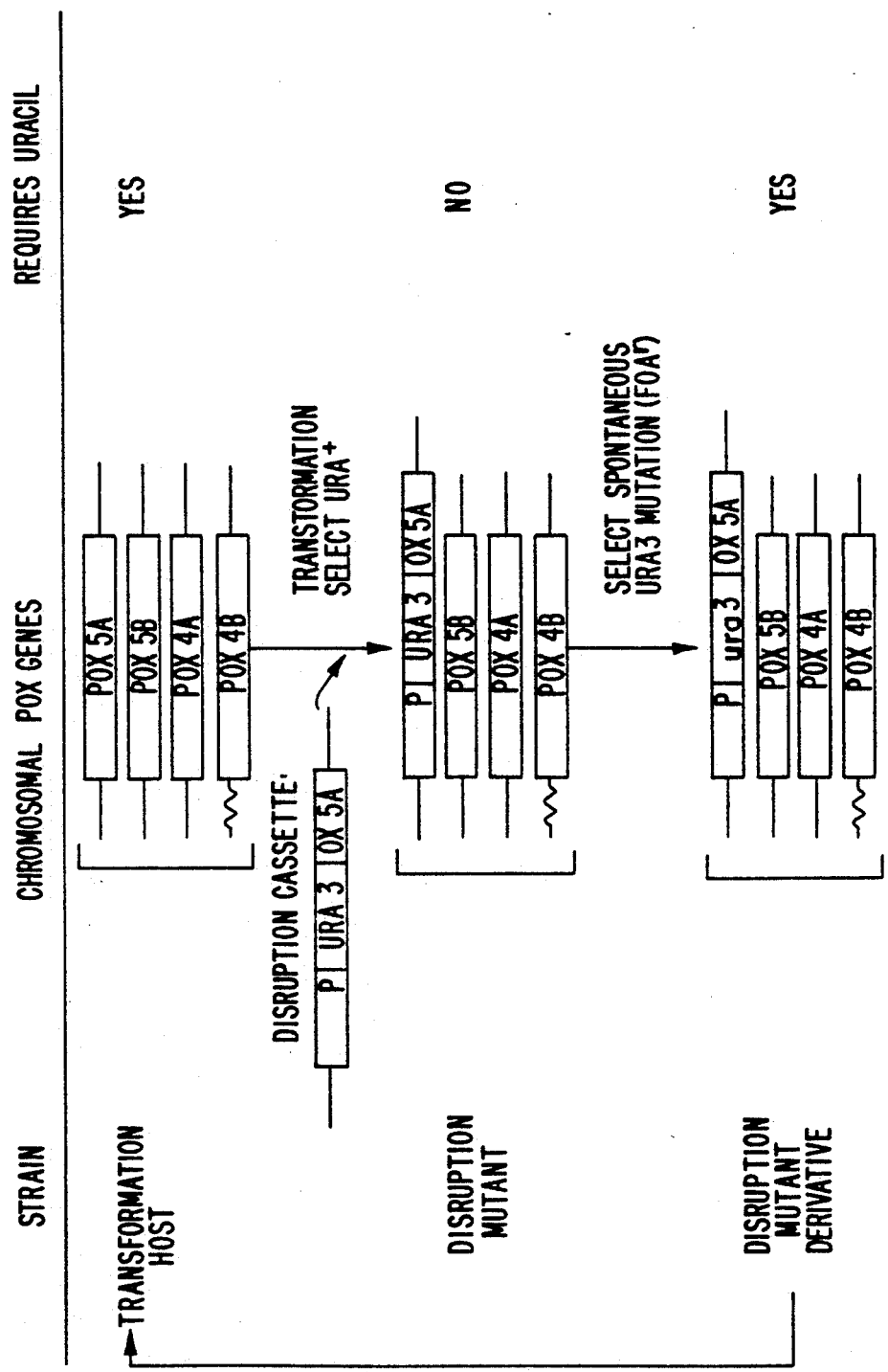
FIG. 2 is a schematic representation of the sequential POX gene disruption process.

One aspect of the present invention provides a general method for the site-specific modification of the *C. tropicalis* genome. The method is based on the use of a gene disruption cassette as a replacement for a chromosomal target gene. The replacement gene is non-functional by virtue of an insertional inactivation with the selectable marker gene. The disruption cassette is a serially arranged linear DNA fragment comprised of, firstly, a DNA fragment which has homology to the native *C. tropicalis* genome, secondly, a selectable marker gene, and thirdly, a DNA fragment which has homology to the native *C. tropicalis* genome. The selectable marker is therefore, flanked on both ends by DNA sequences which are homologous to the native *C. tropicalis* genome. The two flanking sequences are preferably, but not necessarily, contiguous DNA sequences in the undisrupted yeast genome and direct the site of integration of the disruption cassette into the yeast genome.

A disruption cassette can be constructed by subcloning a selectable marker into an isolated target gene. Any type of selectable marker which is extraneous to the target gene can be used to disrupt the target gene. Preferably, the selectable marker is one which confers a particular phenotype to the cell into which the disruption cassette is transformed. Most preferably, the selectable marker confers a prototrophic phenotype to transformed cells which can be reversibly changed to auxotrophy so that the same selectable marker can be subsequently used in multiple gene disruptions in the same strain.

For example, a *C. tropicalis* transformation host which is auxotrophic for a particular pyrimidine is transformed to prototrophy by a disruption cassette containing a functional selectable marker gene required for the synthesis of the particular pyrimidine. The resulting transformants which have been made prototrophic for said particular pyrimidine, are selected by their ability to grow in a medium deficient in the pyrimidine. These transformants contain a targeted gene disruption as the result of the replacement of a functional target gene with a nonfunctional target gene.

This process is preferably used to disrupt the POX4 and POX5 genes of *C. tropicalis* so that the resulting strain can be used to make alpha, omega-dicarboxylic acids. The POX4 and POX5 genes encode distinct subunits of long chain Acyl-CoA oxidase, which are the peroxisomal polypeptides (PXPs) designated PXP-4 and PXP-5, respectively. These PXPs are found in the peroxisomes which are intracellular organelles present in *C. tropicalis* containing various related enzymes which function in the degradation of alkane and fatty acid substrates. Therefore, disruption of the POX4 and POX5 genes encoding these PXPs will effectively block the β-oxidation of fatty acids, thereby redirecting the substrate toward the omega-oxidation pathway while preventing reutilization of the dicarboxylic acid products of the omega-oxidation pathway.

In the preferred process, a *C. tropicalis* transformation host, auxotrophic for uracil (Ura⁻), is transformed to uracil prototrophy with a disruption cassette containing either a URA3A functional gene flanked on one end by a 1.2 Kb of 5'-POX5 sequence and on the other end by a 2.7 Kb of 3'-POX5 sequence or a URA3A functional gene flanked on one end by a 2.1 Kb of 5'-POX4 sequence and on the other end by a 4.5 Kb of 3'-POX4 sequence. The transformed cells are made prototrophic for uracil and are selected by their ability to grow in the absence of uracil. In the former case, one of the POX5 genes of *C. tropicalis* is disrupted and it can no longer encode PXP-5, a distinct isozyme of Acyl-CoA oxidase, while in the latter case, one of the POX4 genes is disrupted and can no longer encode PXP-4, another distinct isozyme of Acyl-CoA oxidase.

Another aspect of the present invention provides a process for restoring an auxotrophic phenotype to cells previously transformed to prototrophy with a selectable marker comprising: first, selecting or screening for spontaneous mutations which inactivate the selectable marker thereby resulting in the isolation of auxotrophic mutants, secondly, confirming the auxotrophic phenotype of the mutants, and thirdly, confirming the parental genotype of the mutants by Southern hybridization to the appropriate gene probes. In this method, spontaneous point mutations which occur within the selectable marker gene restore the auxotrophic phenotype to the disrupted mutants.

In a preferred embodiment, the Ura⁻auxotrophic phenotype is restored to cells previously transformed to Ura⁺prototrophy by first selecting for spontaneously formed Ura- mutants by their ability to grow in a medium containing 5-fluoroorotic acid (5-FOA), an analog of a uracil pathway intermediate which is toxic to Ura⁺cells. Selection in the presence of 5-FOA permits identification of isolates which have a non-functional URA3A selectable marker. The Ura⁻ phenotype of these cells is confirmed by establishing the fact that they do not grow in the absence of uracil. The parental genotype of the cells is confirmed by Southern hybridization to the appropriate gene probe.

Another method of restoring an auxotrophic phenotype to cells previously transformed to prototrophy with a selectable marker utilizes a directed deletion method. In this method, the prototrophic cells are transformed with a non-functional selectable marker gene which has been made non-functional by an in-vitro deletion of at least a portion of the central coding sequence The in-vitro deletion can be accomplished by constructing a plasmid containing the selectable marker gene and linearizing the plasmid with a restriction endonuclease that cuts the selectable marker gene at a unique cleavage site in the central coding sequence. The resulting fragment which contains portions of the restricted selectable marker gene on each end is then exposed to a processive exonuclease which excises nucleotides (bp) from the ends of the fragment to form a new, shorter deletion fragment. This new fragment is then recircularized by ligation to form a new plasmid containing a deletion of the selectable marker or a portion thereof. This plasmid does not contain the unique restriction site that the original plasmid contained since this site was removed by the action of the processive exonuclease. The deleted gene is liberated from the plasmid by cleavage with one or more restriction enzymes that cut the plasmid at the ends of the modified selectable marker gene and is transformed into cells previously made prototrophic with a functional selectable marker gene. The transformed cells are thereby made auxotrophic as the result of the replacement of a functional selectable marker gene with a nonfunctional one. The auxotrophy of these mutants can be confirmed by testing them for inability to grow in the absence of the particular nutrient. The strain genotype of these mutants can be confirmed by screening for the absence of the unique restriction endonuclease site previously present in the selectable marker gene contained within the genome of the host cell.

In a preferred embodiment of the above-disclosed process, the Ura⁻ auxotrophic phenotype is restored to cells previously transformed to Ura⁺ prototrophy with a URA3 selectable marker by restricting a plasmid containing a wild type URA3 gene with KonI. The linear DNA fragment thus obtained is then digested with Bal31 and religated to form a plasmid containing a 50 bp URA3A deletion with 2.4 Kb flanking URA3A homology. The deleted URA3 gene is first liberated as a linear DNA fragment by digestion of the plasmid with EcoRI and PstI and then transformed into Ura⁺ prototrophic host cells (strain H51). Ura⁻ transformants are recovered and their auxotrophy is confirmed by the inability of said transformants to grow in a medium deficient in uracil. The genotype of the Ura⁻ auxotrophic mutants is confirmed by demonstrating the 50 bp chromosomal deletion in the strain H51dKpn chromosome by Southern hybridization to a URA3A gene probe. The 7.1 Kb and 1.4 Kb KpnI fragments of strain H51 are thereby shown to be replaced by an 8.5 Kb KonI fragment in strain H51dKpn.

The foregoing processes can be applied to any selectable marker system which provides for a phenotypic change in the host strain. Other suitable selectable markers include but are not limited to the HIS4, POX4A, POX4B, or POX5 genes. In the case where the selectable marker is a HIS4 gene, a host cell is auxotrophic for histidine or, in the case where all four chromosomal POX genes are inactvated by gene disruption the selectable marker can be one of the four POX genes. In this case, mutants transformed with a POX gene are selected by their ability to grow in media containing alkanes or fatty acid esters as the sole carbon source.

Yet another aspect of the present invention provides a process for completely blocking the β-oxidation pathway in *C. tropicalis* at its first reaction by disrupting the POX4A, POX4B and both POX5 genes of a *C. tropicalis* host strain. The sequence in which the four POX genes are disrupted is immaterial. It is only necessary that all of the POX genes are disrupted. When all of these POX genes of *C. tropicalis* are disrupted, they no longer encode the functional acyl-CoA oxidase isozymes necessary for the β-oxidation pathway. Therefore, the organism can no longer oxidize fatty acids at the β-carbon atom because the enzymes necessary to this pathway are not synthesized. The substrate is therefore redirected toward the omega-oxidation pathway while also preventing degradation of the dicarboxylic acid products through the β-oxidation pathway. Therefore, a *C. tropicalis* strain in which all four POX genes are disrupted will synthesize substantially pure alpha, omega-dicarboxylic acids in substantially quantitative yield because the biosynthetic pathway which produces unwanted side products such as β-hydroxy acids, unsaturated acids, or shorter chain acids is no longer functional.

Still another aspect of the present invention provides a process for producing substantially pure alpha, omega-dicarboxylic acid in substantially quantitative yield comprising culturing *C. tropicalis* strain H5343 in a culture medium containing a nitrogen source, an organic substrate and a cosubstrate. The culture medium can contain any inorganic or organic source of nitrogen normally used in processes for culturing microorganisms. Inorganic nitrogen sources include alkali metal nitrates such sodium or potassium nitrate, ammonium salts such as ammonium sulfate, ammonium chloride, ammonium nitrate, ammonium acetate, etc. Organic nitrogen sources include urea, corn steep liquor, yeast extracts, and other organic nitrogen sources known to those skilled in the art. The organic substrate can be any aliphatic compound wherein at least one of the terminal carbons is a methyl group and which has from about 4 to about 22 carbon atoms. Such compounds include alkanes, alkenes, alkynes, carboxylic acids and their esters, and arenes. Preferred substrates are alkanes having from about 4 to about 22 carbon atoms and fatty acids and their methyl or ethyl esters wherein the acyl portion contains from about 4 to about 22 carbon atoms. The most preferred substrates are dodecane, tridecane, tetradecane, oleic acid, methyl oleate, methyl palmitate, methyl palmitoleate and methyl myristate.

The cosubstrate is selected from the group consisting of glucose, fructose, maltose, glycerol and sodium acetate. The preferred cosubstrate is glucose. A cosubstrate is necessary because the beta-oxidation pathway of $C.$ $tropicalis$ H5343 is totally blocked, and energy is not available from the oxidation of the substrate. Glucose added at a definite rate along with the substrate strikes a balance between providing an energy source for the cells while allowing the partial oxidation of the substrate to an alpha, omega-dicarboxylic acid.

In a preferred embodiment, a fermentation medium comprising 3 g/l peptone, 6 g/l yeast extract, 6.7 g/l Yeast Nitrogen Base (Difco), 3 g/l sodium acetate and 75 g/l glucose is prepared and sterilized by heating to 121° C. at 15 psi. The medium is then inoculated with 2 ml of a 15% glycerol stock culture, and strain H5343 is grown at 30° C. for a time sufficient to produce a maximum cell density. The maximum cell density is determined by measuring the turbidity of the medium as indicated by an absorbance reading of from about 60 to about 70 at a wavelength of 625 mm. The maximum cell density corresponds to a viable cell count of about $1.5 \times 10^9$.

After achieving the maximum cell density, the pH of the medium is then raised from about 7.5 to about 9.5 with preferred value being in the 8.3 to 8.8 range. The cosubstrate is added at a rate from about 0.5 to about 2.5 grams per hour per liter of fermentation broth. The preferred rate of addition of glucose is from about 1.5 to about 1.75 grams per hour per liter of fermentation broth. The substrate is added simultaneously with the cosubstrate (glucose) at such a rate as to maintain the substrate concentration of from about 4 to about 40 grams per liter of fermentation broth. The preferred rate of addition of substrate is from about 10 to about 20 grams per liter of fermentation broth. The fermentation can be continued as described above indefinitely in the case of a continuous process or until the working volume of the fermentation vessel is reached in the case of a batch process.

As disclosed above, the preferred process for making alpha, omega-dicarboxylic acids is by using strain H5343, the strain in which all four POX genes are blocked. Actually, any of the other 9 strains listed in FIG. 4, in which some of the POX genes are blocked, can also be used in the above described process.

The following examples will serve to illustrate but not limit the invention.

EXAMPLE 1

Construction of a POX5 Disruption Cassette

In preparation for the disruption of the $C.$ $tropicalis$ chromosomal POX5 genes, the URA3A selectable marker was subcloned into the isolated POX5 gene contained on plasmid pKD1dBamHI (see Example 22). The POX5 gene has been previously cloned and its DNA sequence determined (Okasaki, K.,et al., (1988) PNAS, USA 83; 1232-1236). For the development of a POX5 disruption vector, 12 ug of plasmid pCU2dSacI (see Example 21) containing the $C.$ $tropicalis$ URA3A gene was linearized by digestion with the NruI restriction endonuclease. BamHT linkers were ligated to these DNA fragments by standard procedures (Maniatis et al., Molecular Cloning: A Laboratory Manual, Cold Spring Harbor, 1982) and following digestion with the BamHI restriction endonuclease, the URA3A gene was liberated on a 2.2 Kb BamHI restriction fragment. The URA3A gene was then ligated to 1.25 ug of BamHI linearized, dephosphorylated pKD1dBamHI plasmid (see Example 22). This plasmid contains the $C.$ $tropicalis$ POX5 gene cloned on a 3.9 Kb EcoRI restriction fragment into the unique EcoRl site of pBR322. To facilitate the URA3A subcloning into the unique POX5 BamHI site, the BamHI site within the tetracycline resistance gene of pBR322 was previously destroyed by filling-in with Klenow polymerase following partial BamHI digestion. The ligation mixture was used to transform $E.$ $coli$ DH5alpha (BRL, Bethesda Maryland, USA) to ampicillin resistance. Restriction analysis of plasmid DNA from 95 ampicillin resistant transformants showed one to contain the expected construction. This plasmid, designated pKD1URA3A, contains the URA3A gene cloned on a 2.2 Kb BamHI fragment into the unique POX5 BamHI restriction site (position #1178) and is flanked by 1.2 Kb of 5'-POX5 sequence and 2.7 Kb of 3'-POX5 sequence. Digestion of the plasmid with the EcoRl restriction endonuclease liberates the 5'-pox5-URA3A-pox5-3' cassette suitable for disruption of the $C.$ $tropicalis$ chromosomal POX5 gene (FIG. 1B).

EXAMPLE 2

Construction of a POX4 Disruption Cassette

In preparation for the disruption of the chromosomal POX4 genes, the URA3A selectable marker was first subcloned into the isolated POX4 gene contained on plasmid pKD3dBamHI (see Example 23). The POX4 gene has been previously cloned and its DNA sequence determined (Okasaki, K.,et al., 1986, PNAS, USA 83; 1232-1236). For the development of a POX4 disruption vector, 12 ug of plasmid pCU2dSacI (see Example 21) was linearized by digestion with the NruI restriction endonuclease. BamHI linkers were ligated to these DNA fragments by standard procedures (Maniatis et al., Molecular Cloning: A Laboratory Manual, Cold Spring Harbor, 1982) and following digestion with BamHI restriction endonuclease, the URA3A gene was liberated on a 2.2 Kb BamHI restriction fragment. The URA3A gene was then ligated to 0.75 ug of BamHI linearized, dephosphorylated pKD3dBamHI plasmid. This plasmid contains the POX4 gene cloned on a 6.6 Kb HindIII fragment into the unique HindIII restriction site of pBR322. To facilitate the URA3A subcloning into the unique BamHI site of the POX4 gene, the BamHI restriction site within the tetracycline resistance gene of pBR322 was previously destroyed by filling-in with Klenow polymerase following partial BamHI digestion. The ligation mixture was used to transform *E. coli* DH5alpha (BRL, Bethesda, Md., USA) to ampicillin resistance. Restriction analysis of plasmid DNA from 92 transformants showed one to contain the expected construction. This plasmid, designated pKD3-URA3A, contains the URA3A gene cloned on a 2.2 Kb BamHI fragment into the unique POX4 BamHI site (pos#2101) and is flanked by 2.1 Kb of 5'-POX4 sequence and 4.5 Kb of 3'-POX4 sequence. Digestion of this plasmid with the EcoRI restriction endonuclease liberates the 5'-pox4-URA3-pox4-3' cassette suitable for disruption of the *C. tropicalis* chromosomal POX4 gene (FIG. 1A).

EXAMPLE 3

Disruption of the *C. tropicalis* Chromosomal POX5 Gene.

*C. tropicalis* strain SU-2 (ATCC 20913) spheroplasts were transformed to uracil prototrophy with EcoRI digested pKD1-URA3A. In this and the following examples, *C. tropicalis* was transformed by the following procedure: A colony of *C. tropicalis* was inoculated into about 10 ml YEPD medium and the culture shaken at 30° C. overnight. Cells were diluted to an absorbance ($A_{600}$) equal to about 0.01–0.1 and the cells maintained in log growth phase in YEPD medium at 30° C. Then 0.03 ml of the culture at an $A_{600}$ of 0.01 was inoculated into 100 ml YEPD medium and the culture shaken at 30° C. overnight. After harvesting the culture at $A_{600}$ 0.2–0.3 by centrifugation at 1500×g for 5 min, the cells were washed 1×10 ml sterile water, 1×10 ml freshly prepared SED (SED=1 M sorbitol, 25 mM EDTA, 50 mM DTT, filter sterilized), 1×10 ml 1 M sorbitol and the cells then resuspended in 5 ml SCE buffer (SCE=1.0 M sorbitol, 100 mM sodium citrate, pH 5.8, 10 mM EDTA). To the mixture was added 20 μl of 4 mg/ml Zymolyase 20000 and the medium was incubated at 30° C. Spheroplast formation was monitored as follows: 100 μl aliquots of cells were added to either 900 μl of 0.2% SDS or 900 μl of 1 M sorbitol. The incubation with the Zymolyase was terminated at the point at which cells lysed in SDS, but not in sorbitol (usually 15–30 min of incubation). Spheroplast formation was efficient, with an estimated 99% of the cells becoming osmotically fragile. At the termination of the incubation, the spheroplasts were washed 1×10 ml 1 M sorbitol by centrifugation at 1,000×g for 10 min, 1×10 ml of sterile CaS (CaS=1 M sorbitol, 10 mM calcium chloride, filter sterilized) and the cells were then resuspended in a total of 0.6 ml of CaS. Transformation was achieved by adding DNA samples (up to 20 μl) to 12×75 mm sterile polypropylene tubes; the DNA was in water or TE buffer. To each DNA sample was added 100 μl of spheroplast and the mixture incubated at room temperature for 20 min. To this mix was then added 1 ml of PEG solution (PEG solution=20% polyethylene glycol - 3350, 10 mM calcium chloride, 10 mM Tris. HCl, pH 7.4, filter sterilized) and incubated at room temperature for 15 min. After centrifuging the samples at 1,000×g for 10 min, the PEG solution was decanted, the samples resuspended in 150 μl of SOS (SOS=1 M sorbitol, 30% YEPD medium, 10 mM calcium chloride, filter sterilized) and the resuspended samples were incubated for 30 min at room temperature To the sample was then added 850 μl of sterile 1 M sorbitol. For regeneration of cells, 10 μl and 990 μl aliquots of each sample were added to 10 ml aliquots of melted regeneration agar held at 50° C. and the mixture poured onto plates containing a solid 10 ml bottom agar layer of regeneration agar. (To prepare regeneration agar autoclave 9 g of bacto-agar and 13.5 g KCl in 240 ml of water, after autcloaving, 30 ml of 20% sterile dextrose and 30 ml of sterile 10X YNB is added and the mixture is then held at 55° C.) 10 ml of bottom layer agar was poured onto plates 30 minutes before the transformation samples were ready. Regeneration of spheroplasts was efficient and was greater than 10%. Transformation of ura3 strains of *C. tropicalis* for example strain SU-2, occurred at a high frequency. The frequency of transformation was about 5,000–20,000 Ura+ colonies per microgram of DNA. Both closed circular and linear plasmid DNAs gave a high frequency of transformation. The efficiency was about 10- to 100-fold less using the LiCl transformation method.

Figure 3:
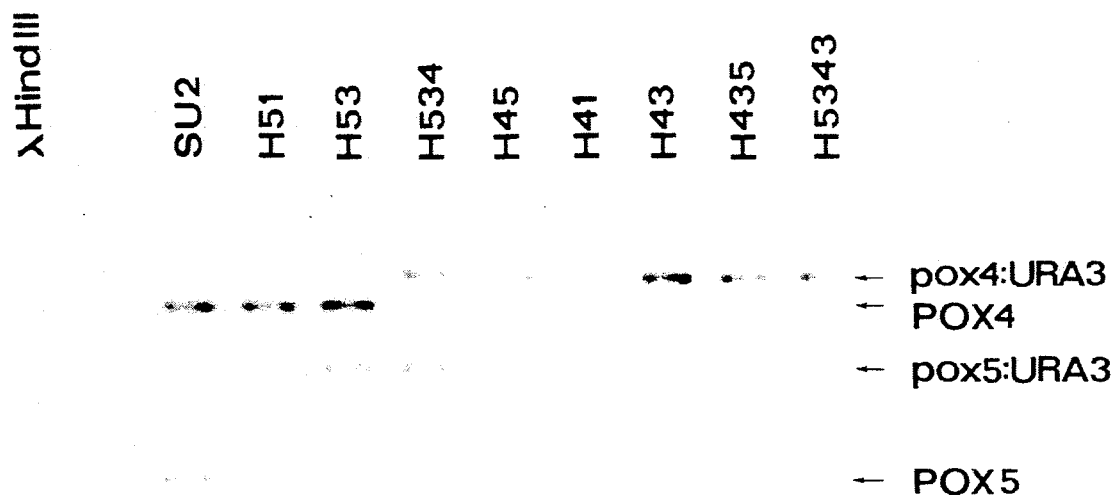
FIG. 3 is an illustration of a Southern hybridization of EcoR1 digested genomic DNA from various transformants to POX4 and POX5 probes.

Following transformation with 5 ug EcoRI digested pKD1-URA3A, approximately 200 mitotically stable Ura+ transformants were recovered. Eleven transformants were subsequently screened for growth on dodecane and by Southern hybridization of EcoRI digested genomic DNA to POX5 and URA3A probes by standard methods (Maniatis et al., Molecular Cloning: A laboratory Manual, Cold Spring Harbor, 1982). All eleven transformants demonstrated growth on dodecane comparable to the wild-type. Hybridization of EcoRI digested genomic DNA from these transformants to a POX5 probe revealed the presence of a 6.1 Kb EcoRI fragment not present in the wild-type (a representative of these transformants, designated as strain H51, is shown in FIG. 3). This fragment is about 2.2 Kb larger than the wild-type POX5 EcoRI fragment (3.9 Kb)(illustrated in FIG. 3 as strain SU-2) and corresponds to the replacement of the wild-type POX5 locus with the POX5-URA3A disruption cassette. This 6.1 Kb EcoRI fragment was also detected with a URA3A probe. However, hybridization to the POX5 probe also "uncovered" the presence of an additional wild-type copy of the POX5 gene (3.9 Kb) in each of these transformants. This EcoRI hybridization pattern could reflect either a tandem integration of the disruption cassette into a haploid POX5 gene or a disruption of a single POX5 gene at a diploid locus. The more intense hybridization of the POX5 probe to the 3.9 Kb POX5 EcoRI fragment in the wild-type suggested that there are normally two copies of the POX5 gene. To distinguish these possibilities, genomic DNA from the transformants was digested with NcoI and analyzed by Southern hybridization as described above. Since there are no internal NcoI sites within the POX5-URA3A disruption cassette, the fragment sizes generated by NcoI digestion depend upon the chromosomal location of the NcoI sites nearest the site of integration. Thus, tandem repeats resulting from single-crossover integration would appear as a single large fragment while a POX5 gene disruption at a diploid locus would yield two fragments The hybridization to a POX5 gene probe demonstrated the presence of two NcoI fragments in each of the transformants while only one was detected, with greater hybridization intensity, in the wild-type. Only the larger of the two fragments in each transformant was detected by hybridization to a URA3A gene probe and corresponds in size to that expected for the replacement of the chromosomal POX5 gene with the POX5-URA3A disruption cassette. This represents the first demonstration of a gene disruption event in *C. tropicalis*. In addition, this is the first unambiguous demonstration that *C. tropicalis* is a diploid yeast and contains two copies of each gene. Furthermore, the results demonstrate the utility of the URA3A transformation system by the ability of the subcloned URA3A gene fragment to complement the SU-2 uracil defect when integrated at a site other than the chromosomal URA3A gene. Thus, the NcoI hybridization pattern clearly established the disruption in these transformants, designated as H51 (pox5:URA3A/POX5/POX4A/POX4B), of a single copy of the POX5 gene at a normally diploid locus. Only one of the two POX5 genes has been functionally inactivated as the result of the gene disruption. Selective disruption of the remaining POX5 gene is necessary to functionally inactivate POX5 activity. All of the transformants analyzed contained the expected POX5 gene disruption at the chromosomal POX5 locus. None of the Ura+ transformants were recovered as the result of integration at the chromosomal URA3A locus.

EXAMPLE 4

Disruption of the *C. tropicalis* Chromosomal POX4 Gene.

*C. tropicalis* strain SU-2 (ATCC 20913) spheroplasts were transformed to uracil prototrophy with 10 ug of EcoRI digested pKD3-URA3A as described in Example 3. Approximately 160 mitotically stable Ura+ transformants were recovered. All demonstrated the ability to utilize either dodecane or methyl laurate for growth. Nine Ura+ transformants were screened by Southern hybridization for site-specific gene disruption as previously described. Hybridization of EcoRI digested genomic DNA from six of these transformants to a POX4 probe revealed the presence of a 13 Kb EcoRI fragment not present in the wild-type (a representative of these transformants is designated as strain H41-FIG. 3)). This fragment is about 2.2 Kb larger than the wild-type POX4 EcoRI fragment (9.8 Kb)(illustrated in FIG. 3 as strain SU-2) and corresponds to the replacement of the wild-type POX4 locus with the POX4-URA3A disruption cassette. This 13 Kb EcoRI fragment was also detected with a URA3A probe in strain H41 but not in strain SU-2. However, hybridization to the POX4 probe also "uncovered" the presence of an additional wild-type copy of the POX4 gene in each of these transformants thus indicating that *C. tropicalis* is also diploid at the POX4 locus. Hybridization of HpaI digested genomic DNA to a POX4 probe indicated that the two chromosomes are heterozygous at this restriction site, thus distinguishing the chromosome into which the transforming DNA had integrated. By comparing the EcoRI and HoaI hybridization patterns, it was determined that, of the nine Ura+ transformants analyzed, two contained precise gene disruption of one POX4 gene, three contained a single crossover integration into one POX4 gene (of which one was a tandem multiple integration), and four contained both a single crossover integration and a gene disruption into one or both chromosomes. The strains containing only precise disruption of one of the POX4 genes were designated as H41 (POX5/POX5/pox4A:URA3A/POX4B)(FIG. 3).

EXAMPLE 5

Regeneration of the URA3 Selectable Marker System.

(A) Selection of Uracil Auxotrophs Resulting From Spontaneous Mutation Within The URA3A Selectable Marker.

*C. tropicalis* SU-2 (Ura−) and H51 (Ura+) were tested for growth in media containing various concentrations of 5-fluoroorotic acid (5-FOA), an analogue of a uracil pathway intermediate which is toxic to Ura+ cells. Both strains were grown to mid-log phase in YEPD medium (2% Bacto-peptone, 2% glucose, 1% Bacto-Yeast Extract) and were plated at various dilutions onto FOA medium (Boeke et al., [1984] Molec. Gen. Genet 197; p345-346) or YEPD medium.

*C. tropicalis* SU-2 demonstrated 71.6%, 50.3% and 14.8% survival in the presence of 500, 750 and 1000 ug/ml 5-FOA, respectively. Under comparable conditions, the Ura+ transformants (H51) demonstrated survival rates of less than $3.6 \times 10^{-6}$. Concentrations of less than 500 ug/ml were found to permit the growth of spontaneous 5-FOA resistant mutants that retained the Ura phenotype. Thus, selection in the presence of 750 ug/ml 5FOA permits identification of isolates which have a non-functional URA3A marker.

EXAMPLE 6

Regeneration of the URA3 Selectable Marker System (B) Directed Chromosomal Deletion Plasmid pCU3dKonI was constructed by progressive Bal31 deletion from the unique KpnI site within the URA3A gene. For these constructions, 10 ug aliquots of plasmid pCU3 were linearized by digestion with KonI restriction endonuclease and were subsequently partially digested with Ba131 nuclease (0.05 U/ug for 5,10,20 or 30 min at 30° C.). Following treatment with DNA polymerase Klenow fragment, the plasmids were recircularized by ligation at low DNA concentration (0.05 ug/ul). The ligation mixtures were used to transform *E. coli* HB101 to ampicillin resistance or were digested with EcoRI and PstI for direct transformation of *C. tropicalis* H51. Three plasmids containing a deletion of the KpnI site and extending toward the BolII sites were recovered from the ampicillin resistant *E. coli* transformants. The deletion cassettes derived from these plasmids can be used to generate relatively small URA3A deletions (bp) while maintaining large stretches of URA3A homology (Kb), and are liberated by digestion of the plasmids with EcoRI and PstI. Strain H51 was transformed with 20 ug of EcoRI/PstI digested pCU3dKonI, previously purified and characterized as containing a 50 bp deletion spanning the URA3A KonI site, by either the LiCl procedure (Ito et al.,[1983] J. Bacteriol. 153;163-168) or the spheroplast procedure. The spheroplast transformation was performed as previously described, except that the spheroplasts were regenerated on the surface of the regeneration medium to facilitate their recovery for subsequent screening. The Ura− isolates were phenotypically identified following nystatin enrichment (described below) and, in some cases, selection for 5-FOA resistance. The cells from the surface of the transfomation plates were pooled by washing with sterile YEPD and were inoculated to a starting $A_{600}$ of 0.1 in YEPD and cultured at 30° C. until an $A_{600}$ of 0.4 was reached. The cells were harvested by centrifugation (5000×g, 5 min) and inoculated into 100 ml of yeast carbon base (YCB; 11 g/L;

Difco) in a sterile 500 ml flask. The culture was shaken at 200 rpm for 21 hours at 30° C. The cells were then centrifuged (5000×g, 5 min), washed once with sterile distilled water and resuspended in 100 ml of minimal medium (yeast nitrogen base 6.7 g/L, dextrose 20 g/L) in 500 ml flasks. The cells were incubated with shaking (200 rpm) at 30° C. for 7 hours. Then, nystatin (50,000 units/ml stock solution in methanol; Sigma #N3503) was added at a final concentration of 35 units/ml and the cells incubated for 35 minutes at 30° C. with shaking (200 rpm). The culture was washed twice with sterile distilled water and resuspended in 10 ml of sterile distilled water. Nystatin-treated cells (0.1 ml aliquots) were plated onto selection plates (YNB 6.7 g/L, dextrose 20 g/L, agar 20 g/L, uracil 50 mg/L, uridine 150 mg/L, uridine 5-phosphate 150 mg/L, 5-fluoroorotic acid 750 mg/L). The plates were incubated for up to two weeks at 30° C., at which time the colonies which grew on the plates were picked with sterile toothpicks and plated onto a second set of selection plates prepared as before. Incubation was for four days at 30° C. The isolates were then transferred to minimal medium plates with or without added uracil. Colonies which could not grow in the absence of uracil were taken for further analysis. Characterization of 25 Ura-isolates recovered from the transformation of H51 spheroplasts with pCU3dKpnI (containing a 50 bp URA3A deletion with 2.4 Kb flanking URA3A homology) by Southern hybridization of EcoRI digested genomic DNA to a POX5 probe showed 13 of the isolates to contain the expected deletion within the disrupted POX5 gene. These strains were designated as H51dKpn (pox-5:duraA/POX5/POX4A/POX4B). The remaining isolates were representative of mitotic recombinants. The 50 bp chromosomal deletion flanking the URA3A KonI site in H51dKpn was further confirmed by Southern hybridization of KonI digested genomic DNA to POX5 and URA3A gene probes. As expected, the 7.1 Kb and 1.4 Kb KonI fragments of H51 detected with the URA3A probe were replaced by an 8.5 Kb KpnI fragment in H51dKpn. The reversion frequencies of several independent H51dKpn isolates were al-1<1×10$^{-8}$.

EXAMPLE 7

Regeneration of the URA3 Selectable Marker System

C. Spontaneous Mutation within the URA3A Selectable Marker: Construction of Strain H53 (pox5:ura3A/pox5:URA3A/POX4A/POX4B)

Strain H53 (pox5:ura3A/pox5:URA3A/POX4A/POX4B) was isolated following transformation of a Ura$^-$ derivative of H51 (H51Ura-) with the POX5-URA3A disruption cassette from pKD1-URA3A to Ura+ as follows: Several spontaneous 5-FOA resistant isolates recovered from H51 in the absence of transforming DNA were found to be identical to H51 in their POX5 EcoRI hybridization pattern but were phenotypically Ura-. The strains were designated H51Ura-(pox5-:ura3A/POX5/POX4A/POX4B). It was reasoned that these derivatives might represent spontaneous point mutations within the URA3A gene at the disrupted POX5 locus and could thus be retransformed with the URA3A selectable marker or, in particular, with the POX5-URA3A disruption cassette to effectively inactivate the remaining functional POX5 gene. Therefore, 20 isolates with a Ura- phenotype and an H51 hybridization pattern were separately transformed to Ura+ with 10 ug of EcoRI digested pKD1-URA3A. Three strains had reversion frequencies (to a Ura+ phenotype) which were low enough to permit easy identification of Ura+ transformants. Characterization of 28 Ura+ transformants from these three strains by Southern hybridization of EcoRI digested genomic DNA to a POX5 probe identified 9 transformants which demonstrated the sole presence of a 6.1 Kb EcoRI fragment with twice the hybridization intensity of H51. These transformants, which have been designated H53 (pox5-:ura3A/pox5:URA3A/POX4A/POX4B), represent disruption of both copies of the POX5 gene and are illustrated in FIG. 3. These strains are capable of growth on dodecane as the sole carbon source. The remaining transformants were identical to H51 and may have resulted from either reversion, gene conversion or by gene relacement at the original disrupted POX5 gene.

EXAMPLE 8

Development of Strain H534

(pox5:ura3A/pox5:ura3A/pox4A:URA3A/POX4B)

This strain, which has both copies of POX5 and one copy of POX4 disrupted was developed by the procedures described above. Ura$^-$: derivatives of H53 (H53Ura$^-$ pox5:ura3A/pox5:ura3A/POX4A/POX4B) were isolated and characterized as described above and then transformed to Ura+ with the POX4 disruption cassette from pKD3-URA3A. Fifty percent of the Ura+ transformants screened by Southern hybridization to both POX4 and POX5 probes had the expected POX4 disruption (H534-FIG. 3). FOA, Ura$^-$ derivatives with low URA+ reversion frequency were obtained from this mutant (designated H534 Ura$^-$: pox5-:ura3A/pox5:ura3A/pox4A:ura3A/POX4B) in preparation for disruption of the remaining functional POX4 gene.

EXAMPLE 9

Development of Strain H45

(pox5:URA3A/POX5/pox4A:ura3A/POX4B)

This strain, which has one copy of both the POX4 and POX5 genes disrupted, was also developed by the procedures described above. Several FOA resistant, Ura$^-$ derivatives from Strain H41 which demonstrated Ura+ reversion frequencies<2×10$^{-7}$ were isolated and screened by Southern hybridization to a POX4 probe for an EcoRI restriction pattern identical to H41. Several candidates, presumably containing a point mutation within the URA3A gene at the disrupted POX4 locus, were recovered and designated as H41Ura-(POX5/POX5/pox4A:ura3A/POX4B).

Strain H45 was isolated following transformation of H41ura- with the POX5 disruption cassette from pKD1-URA3A. All Ura+ transformants analyzed by Southern hybridization to a POX5 probe contained the expected POX5 disruption (H45 - FIG. 3).

EXAMPLE 10

Development of Strain H41B
(POX5/POX5/POX4A/pox4B:URA3A)

To inactivate POX4B, SU-2 was transformed to Ura+ with a truncated POX4A disruption cassette lacking nonhomologous flanking sequences, depending primarily on homologous sequences within the structural gene to direct the mutagenesis. To prepare POX4A for this transformation, the usual 8.3 Kb EcoRl disruption cassette from pKD3URA3 was digested with Bal31 and SalI to generate fragments of approximately 5 Kb and comprized mostly of structural gene sequences flanking the URA3A selectable marker. This DNA was used to transform SU-2 to Ura+. One of the 20 SU-2 transformants screened by Southern hybridization of HoaI digested genomic DNA to a POX4A probe had the expected POX4B disruption. This strain, designated as H41B (POX5/POX5/POX4A/pox4B:URA3A), was confirmed by Southern hybridization of EcoRI or HoaI digested genomic DNA to POX4A, URA3A and pBR322 probes. The EcoRI hybridization profile of this strain is identical to that of H41 as illustrated in FIG. 3. 5FOA-resistant, uracil requiring derivatives from H41B (H41BUra-POX5/POX5/POX4A/pox4B:ura3A) were prepared for the construction of the double POX4 mutant, H43.

EXAMPLE 11

Development of Strain H43

(POX5/POX5/pox4A:URA3A/pox4B:ura3A)

This strain, which contains a disruption of both POX4 genes, was isolated following transformation of H41BUra− to Ura+ with the POX4A disruption cassette from pKD3-URA3A. Seven of the 20 Ura+ transformants screened by Southern hybridization of HoaI digested genomic DNA to a POX4A probe had the expected construction, as illustrated in FIG. 3.

EXAMPLE 12

Development of Strain H534B (pox5:ura3A/pox5:ura3A/POX4A/pox4B:URA3A)

This strain, which contains a disruption of both POX5genes as well as the POX4B gene, was developed as described above. This strain was isolated following transformation of a uracil-requiring derivative of H53 (H53Ura−) with a truncated POX4A-based disruption cassette in order to target the POX4B gene. Two of the 23 URA+ transformants screened by Southern hybridization of SacI digested genomic DNA to a POX4A probe had the expected POX4B gene disruption. The EcoRI hybridization pattern of H534B is identical to H534 as illustrated in FIG. 3.

EXAMPLE 13

Development of Strain H435

(pox5:URA3A/POX5/pox4A:ura3A/pox4B:ura3A)

This strain, which has both POX4 genes and one POX5gene disrupted, was constructed by transformation of a uracil-requiring derivative of H43 (H43Ura−) with the POX5disruption cassette from EcoRI digested pKDl-URA3A. Eight of the 10 Ura+transformants screened by Southern hybridization of EcoRl digested genomic DNA to a POX5 probe had the expected construction, as illustrated in FIG. 3.

EXAMPLE 14

Development of Strain H5343

(pox5:ura3A/pox5:ura3A/pox4A:ura3A/pox-4B:URA3A)

This strain, in which all POX4 and POX5 genes have been inactivated, was isolated following transformation of a uracil-requiring derivative of H534 (H534Ura-) to Ura+ with the truncated POX4A-based disruption cassette from pKD3-URA3A. Three of the 100 transformants screened by Southern hybridization of SacI digested genomic DNA to a POX4A probe contained a disruption of the POX4B gene (FIG. 3). Further evaluation of H5343 by Southern hybridization to a POX5 probe confirmed retention of all previous disruptions. Unlike all previous mutants in the lineage, H5343 can no longer utilize dodecane or methyl laurate as a sole carbon source for growth.

EXAMPLE 15

Production of 1,12-dodecanedioic acid by fermentation of dodecane or methyl laurate with strain H534.

Fermentation of dodecane with strain H53 under the standard fermentation conditions (Example 20) produced approximately 138 g/l 1,12-dodecanedioic acid within 232 hrs with a substrate conversion efficiency of 34%. The final production rate was 0.55 g/l/h. The product was 85.7% dodecanedioic acid with the remainder comprised mostly of adipic acid.

EXAMPLE 16

Production of 1,12-dodecanedioic acid by fermentation of dodecane or methyl laurate with strain H534.

Fermentation of dodecane with strain H534 under the standard fermentation conditions (Example 20) produced approximately 139 g/l within 233 hrs with a substrate conversion efficiency of 32.1%. The final production rate was 0.58 g/l/hr. The product was 82.7% dodecanedioic acid. The remaining product was predominantly adipic acid. With methyl laurate as the substrate, H534 produced 115.3 g/l dicarboxylic acid within 223 hrs with a substrate conversion efficiency of 34.6%. The production rate was 0.49 g/l/hr. The product was 89.1% dodecanedioic acid. The remaining product was predominantly adipic acid.

EXAMPLE 17

Production of dicarboxylic acids by fermentation with strain H5343.

The H5343 fermentations were carried out according to the standard fermentation conditions (Example 20) with the exception that a 30% (v/v) glucose cosubstrate was added during the production phase at levels from 6 g/h to 15 g/h. Dodecane, tridecane, tetradecane or methyl myristate substrates were added according to the standard fermentation procedure during the production phase.

With dodecane (99.0% purity) as the substrate, this strain produced 127 g/l dicarboxylic acid within 232 hrs with a substrate conversion efficiency of 80%. The maximum productivity during the fermentation was 0.9 g/l/hr. The product was 98.4% dodecanedioic acid.

With tridecane (99.0% purity) as the substrate, this strain produced 101.8 g/l dicarboxylic acid within 114 hrs with a substrate conversion efficiency of 92%. The maximum productivity during the fermentation was 1.2 g/l/hr. The product was 98.6% Brassylic acid.

With tetradecane (99.0% purity) as the substrate, this strain produced 103 g/l dicarboxylic acid within 160 hrs with a substrate conversion efficiency of 96%. The maximum productivity during the fermentation was 0.85 g/l/hr. The product was 98.0% tetradecanedioic acid.

With methyl myristate (95% purity) as the substrate, this strain produced 213 g/l dicarboxylic acid within 213 hrs with a substrate conversion efficiency of 99.5%.

The maximum productivity during the fermentation was 1.33 g/l/hr. The product was 94.5% tetradecanedioic acid.

GENERAL EXPERIMENTAL PROCEDURES

EXAMPLE 18

Strain Evaluation

A. Mitotic Stability of strain H5343

To determine the mitotic stability of the POX gene disruptions, Strain H5343 was cultured by successive transfer in YEPD medium (2% glucose, 2% peptone, 1% yeast extract) and assayed daily over a period of 10 days for "reversion" to an alkane-utilizing phenotype by plating 0.1 ml aliquots onto Yeast Nitrogen Base Agar (Difco) containing dodecane as the sole carbon source as well as serial dilutions onto YEPD medium (to obtain viable cell counts for determination of the total number of generations). After 91 generations, no alkane utilizing isolates were recovered, attesting to the stability of this mutant.

EXAMPLE 19

B. Enzymatic Assay for Acyl-CoA Oxidase Activity

A biochemical evaluation of the strains by assay for acyl-CoA oxidase activity was completed. For each strain, inocula were grown for 30 hrs in a glucose based medium (YEPD) followed by a 40 hr induction period in Yeast Nitrogen Base media (Difco) containing yeast extract (0.3%) and either glucose (1.5%), dodecane (1.5%) or methyl laurate (1.5%). Extracts were prepared by repeated passage of washed cell suspensions through a French Pressure Cell (1260 psi) and cell debris was removed by centrifugation (13,000 × g). Activity was measured according to the procedures described by Shimuzu et al., 1979, Biochem. Biophys. Res. Commun. 91, 108–113. Activity was measured independently on C6-CoA, C10-CoA and C12-CoA substrates and normalized to the protein concentration. Some mutants containing partial β-oxidation blockage apparently compensated for the loss of one POX gene product by overexpression of the remaining functional POX genes, resulting in acyl-CoA oxidase activities greater than the control strain, SU-2. However, despite the elevated level of acyl-CoA oxidase in these mutants, a significant portion of the substrate is redirected to the omega-oxidation pathway (see below). This indicates that the POX gene products are neither functionally identical nor physiologically self-sufficient.

Strain H43 allows assessment of POX5 isozyme function. Extracts from this strain demonstrated less activity than SU-2 on all three substrates in methyl-laurate induced cells and on C6-CoA in dodecane induced cells. The specific activities were greater on C12-CoA than on either C10-CoA or C6-CoA. Thus, POX5 isozyme has a "long chain activity" function. In contrast, analysis of H53 has indicated that POX4 isozyme functions over a broader substrate range with the highest specific activities on the shorter chain substrates. The specific activities on C6-CoA or C10-CoA substrates were greater than on C12-CoA. These results indicated that the POX4 and POX5 isozymes differ in chain length specificity. When induced with glucose, only mutants containing POX4 isozyme demonstrated functional acyl-CoA oxidase activity. This indicates that POX4 protein is the sole constituitively expressed acyl-CoA oxidase isozyme. The level of activity is reduced below wild-type levels only in mutants containing POX4 disruptions and thus lacking at least some POX4 protein. Little or no activity was detected in H43 grown on glucose suggesting that POX5is not expressed under these conditions.

No acyl-CoA oxidase activity was detected in H5343 (on substrates ranging from C4-CoA through C18-CoA) confirming that all genes encoding functional acyl-CoA oxidase have been inactivated. Since this mutant can no longer grow on alkane or fatty acids substrates as the sole carbon source, the multiple gene disruptions described herein have resulted in a complete blockage of the β-oxidation pathway.

EXAMPLE 20

Standard Fermentation Procedure

Fermentations were carried out in a 15 L fermentor vessel (Biostat E, B. Braun, Inc) in less than 10 L of culture and under BLI containment precautions and with good laboratory practices as specified in the NIH guidelines for research involving recombinant DNA molecules.

The fermentation medium contained 3 g/l peptone, 6 g/l yeast extract, 6.7 g/l Yeast Nitrogen Base (Difco), 3 g/l sodium acetate and 75 g/l glucose. The medium was sterilized by heating to 121° C. at 15 psi. The seed culture, inoculated with 2 ml of a 15% glycerol stock culture, was prepared in 500 ml of this medium for 24 hrs at 30° C., 250 rpm prior to inoculation into the fermentor vessel. Following inoculation, the culture was maintained at pH8.3 (by the controlled addition of 6N KOH), 80% dissolved oxygen (2 vvm gassing rate and 500–1200 rpm) at 30° C. until an absorbance of from about 60 to about 70 was reached at 625 nm (about 24 hrs) before the addition of the organic substrate. During the initial phase of the fermentation the glucose was exhausted by the culture. Substrate and cosubstrate were then added on a daily basis to maintain a concentration ranging from 4–60 g/l of the organic substrate. The cosubstrate was added at a rate of from about 1.5 to about 1.75 grams per hour per liter of fermentation broth. A commercial antifoam was also added to the fermentor as necessary. Samples were removed on a daily basis to assess levels of product and remaining substrate by gas chromatography.

EXAMPLE 21

Construction of plasmid pCU2dSacI

A 5.8 kb DNA fragment containing the URA3A gene was obtained from the YEp13-based *C. tropicalis* genomic library plasmid, pCU1 (ATCC 67867). To facilitate restriction enzyme mapping of this fragment, most of the fragment was subcloned into pUC19 which is a small (2,686 basepair) pBR322- and M13mp19-based cloning vector containing a multiple cloning site, or polylinker (Yanisch-Perron, C. et al., Gene (1985) 33:103–119). To construct this plasmid, a 6.2 kb EcoRI fragment from pCU1 containing mostly *C. tropicalis* DNA was inserted into the EcoRI site of pUC19, to produce plasmid pCU2. One end of the subcloned fragment contained 377 base pairs of YEp13, and the other stopped at an EcoRI site located approximately 50 base pairs from the right hand BamHI-Sau3AI junction. To construct pCU2dSacI, the 2.8 Kb EcoRI/SacI restriction fragment from pCU2 was subcloned into the EcoRI/SacI sites in the polylinker sequences of pUC19.

EXAMPLE 22

Construction of Plasmid pKD1dBamHl

The *C. tropicalis* POX5 gene was first subcloned on a 3.9 Kb EcoRI restriction fragment from plasmid pC50 (obtained from Prof. T. Kamiryo, Hiroshima University, Hiroshima, Japan) into the unique EcoRI site of pBR322 by standard procedures (Maniatis et al, Molecular Cloning: A Laboratory Manual, Cold Spring Harbor, 1982) to generate the plasmid designated pKD1. To facilitate in-vitro disruption of the subcloned POX5 gene, by insertional inactivation with a selectable marker gene such as the *C. tropicalis* URA3A gene, by subcloning into the unique POX5BamHI site (position #1178), an interfering BamHI site located in the tetracycline resistance gene of pBR322 was destroyed by partial digestion of pKD1 with BamHI restriction endonuclease followed by filling-in of the cohesive ends with DNA polymerase and intramolecular blunt-end ligation. The ligated DNA was used to transform *E. coli* HB101 to ampicillin resistance and an analysis of the plasmids from 5 ampicillin resistant, tetracycline sensitive transformants showed that two of them contained the expected construction. BamHI digestion of the plasmid, designated pKD1dBamHI, yields a single linear restriction fragment suitable for the subcloning of the *C. tropicalis* URA3A gene into the unique POX5 BamHI site.

EXAMPLE 23

Construction of Plasmid pKD3dBamHl

The C. tropicalis POX4 gene was first subcloned on a 6.6 Kb HindIII restriction fragment from plasmid pCl (obtained from Prof. T. Kamiryo, Hiroshimma University, Hiroshima, Japan) into the unique HindIII site of pBR322 by standard procedures (Maniatis et al, Molecular Cloning: A Laboratory Manual, Cold Spring Harbor, 1982) to generate the plasmid designated pKD3. To facilitate in-vitro disruption of the subcloned POX4 gene, by insertional inactivation with a selectable marker gene and in particular, the *C. tropicalis* URA3A gene, by subcloning into the unique POX4 BamHI site (position #2101), an interfering BamHl site located in the tetracycline resistance gene of pBR322 was destroyed by partial digestion of pKD3 with BamHl restriction endonuclease followed by filling-in of the cohesive ends with DNA polymerase (Klenow) and intramolecular blunt-end ligation. The ligated DNA was used to transform *E. coli* HB101 to ampicillin resistance and an analysis of the plasmids from ampicillin resistant, tetracycline sensitive transformants yielded the desired construction. BamHl digestion of the plasmid, designated pKD3dBamHl, yields a single linear restriction fragment suitable for the subcloning of the *C. tropicalis* URA3A gene into the unique POX4 gene.

DEPOSIT OF MICROORGANISMS

Living cultures of strain SU-2 (ATCC 20913), *E. coli* (HB101) containing plasmid pCUl (ATCC 67867), and strain H5343 (ATCC 20962) have been deposited with American Type Culture Collection, 12301 Parklawn Drive, Rockville, Md. 20852, Oct. 25, 1989, under the Budapest Treaty on the International Recognition of the Deposit of Microorganisms for the purposes of patent procedure.

What is claimed is:

1. A process for the site-specific modification of the *C. tropicalis* genome comprising: (1) transforming a *C. tropicalis* host which is auxotrophic for uracil to prototrophy by disrupting through homologous recombination a target gene selected from the group consisting of the POX4A, POX4B, POX5 and combinations thereof with a linear DNA fragment comprised of a *C. tropicalis* URA3 selectable marker gene wherein said selectable marker gene which is flanked on both ends by DNA sequences having homology to said target gene; (2) selecting the transformants produced in -top (1) for prototrophy by the ability of said transformants to grow in a medium deficient in uracil.

2. The process of claim 1 wherein said linear DNA fragment is URA3A gene flanked on a first end by a 1.2 Kb 5'POX5 sequence and on a second end by a 2.7 Kb 3'POX5 sequence.

3. The process of claim 1 wherein said linear DNA fragment is URA3A gene flanked on a first end by a 2.1 Kb 5'POX5 sequence and on a second end by a 4.5 Kb 3'POX4 sequence.

4. A process for restoring uracil auxotrophy to *C. tropicalis* cells previously transformed to prototrophy with a URA 3 selectable marker comprising the steps of: (a) selecting or screening for spontaneous mutations which inactivate said selectable marker, (b) confirming the uracil auxotrophy of said mutants, (c) confirming the parental genotype of the uracil auxotrophs by Southern hybridization to appropriate gene probes.

5. A process for restoring uracil auxotrophy to *C. tropicalis* cells previously transformed to prototrophy with a URA 3 selectable marker comprising the steps of: (a) transforming prototrophic host cells with a non-functional URA3 selectable marker gene which has been made non-functional by an in-vitro deletion of a portion of the central coding sequence of said gene to produce auxotrophic mutants, (b) confirming the uracil auxotrophy of said mutants, (c) confirming the uracil auxotrophy of said mutants, (c) confirming the parental geneotype of the uracil auxotrophs by Southern hybridization to appropriate gene probes.

6. The process of claim 5 wherein said prototrophic cells are obtained following transformation of a ura3 auxotroph of *C. tropicalis* with a URA3A selectable marker gene and wherein said non-functional selectable marker gene is derived from the *C. tropicalis* URA3A.

7. A process for completely blocking the β-oxidation pathway in *C. tropicalis* at its first committed reaction comprising disrupting through homologous recombination of the POX4A, POX4B, and both POX5 target genes with a linear DNA fragment comprised of a URA3A selectable marker gene wherein said selectable marker gene is flanked on both ends by DNA sequences having homology to said target genes of a *C. tropicalis* host strain.

8. A *Candida tropicalis* cell having a disrupted chromosomal POX4A gene wherein said POX4A gene is disrupted through homologous recombination with a linear DNA fragment comprised of a URA3A selectable marker gene wherein said selectable marker gene is flanked on both ends by DNA sequences having homology to said POX4A gene of a *C. tropicalis* host strain.

9. A *Candida tropicalis* cell having a disrupted chromosomal POX4B gene wherein said POX4B gene is disrupted through homologous recombination with a linear DNA fragment comprised of a URA3A selectable marker gene wherein said selectable marker gene is flanked on both ends by DNA sequences having homology to said POX4B gene of a *C. tropicalis* host strain.

10. A *Candida tropicalis* cell having a disrupted chromosomal POX5 gene wherein said POX5 gene is disrupted through homologous recombination with a linear DNA fragment comprised of a URA3A selectable marker gene wherein said selectable marker gene is flanked on both ends by DNA sequences having homology to said POX5A gene of a *C. tropicalis* host strain.

11. A *Candida tropicalis* cell wherein the chromosomal POX4A and one of the chromosomal POX5 genes are disrupted wherein said POX4A and one of said chromosomal POX5 genes are disrupted through homologous recombination with a linear DNA fragment comprised of a URA3A selectable marker gene wherein said selectable marker gene is flanked on both ends by DNA sequences having homology to said POX4A and one of said chromosomal POX5 genes of a *C. tropicalis* host strain.

12. A *Candida tropicalis* cell having a disrupted chromosomal POX4A and POX4B genes wherein said POX4A and POX4B genes are disrupted through homologous recombination with a linear DNA fragment comprised of a URA3A selectable marker gene wherein said selectable marker gene is flanked on both ends by DNA sequences having homology to said POX4A and POX4B genes of a *C. tropicalis* host strain.

13. A *Candida tropicalis* cell wherein both copies of the chromosomal POX5 gene are disrupted through homologous recombination with a linear DNA fragment comprised of a URA3A selectable marker gene wherein said selectable marker gene is flanked on both ends by DNA sequences having homology to both of said POX5 genes of a *C. tropicalis* host strain.

14. A *Candida tropicalis* cell wherein both copies of the chromosomal POX5 gene and the chromosomal POX4A genes are disrupted through homologous recombination with a linear DNA fragment comprised of a URA3A selectable marker gene wherein said selectable marker gene is flanked on both ends by DNA sequences having homology to both of said POX5 genes and said POX4A gene of a *C. tropicalis* host strain.

15. A *Candida tropicalis* cell wherein both copies of the chromosomal POX5 gene and the chromosomal POX4B genes are disrupted through homologous recombination with a linear DNA fragment comprised of a URA3A selectable marker gene wherein said selectable marker gene is flanked on both ends by DNA sequences having homology to both of said POX5 genes and said POX4B gene of a *C. tropicalis* host strain.

16. A *Candida tropicalis* cell wherein both copies of the chromosomal POX5 gene and the chromosomal POX4A and POX4B genes are disrupted through homologous recombination with a linear DNA fragment comprised of a URA3A selectable marker gene wherein said selectable marker gene is flanked on both ends by DNA sequences having homology to both of said POX5 genes and both of said POX4A and POX4B genes of a *C. tropicalis* host strain.

17. A process for producing a substantially pure alpha, omega-dicarboxylic acid in substantially quantitative yield comprising culturing *C. tropicalis* strain H5343 in a culture medium containing a nitrogen source, an organic substrate and a cosubstrate.

18. The process of claim 17 wherein the initial pH of said culture medium is about 6.5.

19. The process of claim 17 wherein the pH of said culture medium after maximum cell density is reached is maintained at from about 8.3 to about 8.8.

20. The process of claim 17 wherein the concentration of said substrate in said culture medium is from about 10 to about 20 grams per liter.

21. The process of claim 17 wherein said cosubstrate is added at a rate of from about 1.5 to about 1.75 grams per hour per liter of alkaline medium.

22. The process of claim 17 wherein said substrate is an alkane having from about 4 to about 22 carbon atoms.

23. The process of claim 22 wherein said alkane is dodecane, tridecane, or tetradecane.

24. The process of claim 23 wherein said alkane is dodecane.

25. The process of claim 17 wherein said substrate is an ester wherein the acyl portion of said ester has from about 4 to about 22 carbon atoms.

26. The process of claim 25 wherein said ester is a methyl or ethyl ester of a fatty acid wherein the acyl portion of said ester has from about 12 to about 18 carbon atoms.

27. The process of claim 26 wherein said ester is methyl myristate, methyl palmitate, methyl palmitoleate or methyl oleate.

28. The process of claim 17 wherein said substrate is a carboxylic acid having from about 4 to about 22 carbon atoms.

29. The process of claim 28 wherein said fatty acid has from about 12 to about 18 carbon atoms.

30. The process of claim 29 wherein said fatty acid is oleic acid.

* * * * *